US012270882B2

(12) United States Patent
Yang et al.

(10) Patent No.: US 12,270,882 B2
(45) Date of Patent: Apr. 8, 2025

(54) IMAGING SYSTEM AND METHOD

(71) Applicant: GE Precision Healthcare LLC, Wauwatosa, WI (US)

(72) Inventors: Jingyi Yang, Beijing (CN); Mingyang Yang, Beijing (CN); Yanran Xu, Beijing (CN); Yuting Dou, Beijing (CN); Bingjie Zhao, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 367 days.

(21) Appl. No.: 17/752,070

(22) Filed: May 24, 2022

(65) Prior Publication Data

US 2022/0381862 A1 Dec. 1, 2022

(30) Foreign Application Priority Data

May 31, 2021 (CN) .......................... 202110600353.5

(51) Int. Cl.
*G01R 33/56* (2006.01)
*G06T 7/13* (2017.01)
(Continued)

(52) U.S. Cl.
CPC ..... *G01R 33/5608* (2013.01); *G01R 33/5601* (2013.01); *G06T 7/13* (2017.01);
(Continued)

(58) Field of Classification Search
None
See application file for complete search history.

(56) References Cited

U.S. PATENT DOCUMENTS

2010/0249582 A1 9/2010 Feuerlein
2020/0005463 A1* 1/2020 Wu .......................... G06T 7/149
(Continued)

FOREIGN PATENT DOCUMENTS

CN 107358600 A 11/2017
CN 107578416 A * 1/2018
(Continued)

OTHER PUBLICATIONS

CN 111968112—English Abstract obtained from Espacenet.com; 1 page.
(Continued)

*Primary Examiner* — Jiangeng Sun

(57) ABSTRACT

The present disclosure relates to an imaging system and method. Specifically, an imaging system comprises: a positioning image acquisition unit, configured to acquire a positioning image of a scanning object; a monitoring slice image acquisition unit, configured to determine a key point corresponding to the position of a target region of interest in the positioning image by using a neural network, and acquire a monitoring slice image of the scanning object at the position of the key point; and a target region-of-interest segmentation unit, configured to segment the monitoring slice image to obtain the target region of interest. The present disclosure can accurately acquire the position of the monitoring slice, and can accurately obtain the target region of interest through segmentation by a cascaded coarse segmentation and fine segmentation.

11 Claims, 14 Drawing Sheets

(51) Int. Cl.
  *G06T 7/136*  (2017.01)
  *G06T 7/155*  (2017.01)
  *G06V 10/25*  (2022.01)

(52) U.S. Cl.
  CPC .............. *G06T 7/136* (2017.01); *G06T 7/155* (2017.01); *G06V 10/25* (2022.01); *G06T 2207/10088* (2013.01); *G06T 2207/20084* (2013.01)

(56) References Cited

U.S. PATENT DOCUMENTS

2020/0272841 A1* 8/2020 Han ................. G06T 7/0012
2020/0380680 A1  12/2020 Aoyagi
2021/0259654 A1* 8/2021 Yao ................... A61B 6/488
2021/0386389 A1* 12/2021 Freiman ............ A61B 6/504

FOREIGN PATENT DOCUMENTS

| | | |
|---|---|---|
| CN | 108665462 A | 10/2018 |
| CN | 110909756 A | 3/2020 |
| CN | 111968112 A | 11/2020 |
| CN | 110310287 B | 4/2022 |
| EP | 3649955 A1 * | 5/2020 ............ A61B 6/032 |
| JP | 2020192006 A | 12/2020 |

OTHER PUBLICATIONS

JP application 2022-084192 filed May 24, 2022—Office Action issued Jul. 12, 2023; Machine Translation; 4 pages.

\* cited by examiner

IMAGING SYSTEM AND METHOD

CROSS-REFERENCE TO RELATED APPLICATIONS

This application claims priority to Chinese Patent Application No. 202110600353.5, filed on May 31, 2021, the disclosure of which is incorporated herein by reference in its entirety.

TECHNICAL FIELD

The present disclosure relates to medical imaging, and in particular to an imaging system and method for contrast enhancement scanning.

BACKGROUND

Contrast enhancement (CE) scans usually refer to medical imaging scans in which contrast agents are injected intravenously, such as computed tomography (CT) scans and magnetic resonance imaging (MRI) scans. Contrast enhancement scanning increases the density difference between tissues and lesions, and can more clearly show the relationship between a lesion and surrounding tissues, as well as the size, shape, and extent of the lesion, and help to find lesions that are not displayed or unclear in plain scans, and can also be utilized to dynamically observe the distribution and excretion of a contrast agent in a certain organ or lesion and determine the nature of the lesion according to characteristics thereof.

Common CT-enhanced scans such as computed tomography angiography (CTA) use a bolus tracking method to obtain excellent image quality. The bolus tracking method includes setting a monitoring region of interest (ROI) in a target vessel region in a monitoring layer before a CTA scan, after starting a contrast agent injection, performing a low dosage scan on the monitoring layer at a certain time interval, and automatically or manually triggering a volume scan after a CT value in the ROI reaches a threshold. The positions of the monitoring layer and the monitoring region of interest affect the image quality of the CTA examination. Currently, the monitoring layer and the monitoring region of interest are usually manually set by an imaging technician. On the one hand, the accuracy of the setting and the image quality depend on the experience of the imaging technician; on the other hand, the workload of the imaging technician is increased.

Therefore, there is a need for a novel imaging system and method that can automatically and accurately set a monitoring layer and a monitoring region of interest to improve enhanced contrast imaging quality.

SUMMARY

In view of the above technical problems, an embodiment of the present application provides an imaging system, which includes a positioning image acquisition unit configured to acquire a positioning image of a scanning object, a monitoring slice image acquisition unit configured to determine a key point corresponding to the position of a target region of interest in the positioning image by using a neural network and acquire a monitoring slice image of the scanning object at the position of the key point, and a target region-of-interest segmentation unit, configured to segment the monitoring slice image to obtain the target region of interest.

In one aspect of the present disclosure, the neural network includes a residual neural network.

In one aspect of the present disclosure, the target region of interest is used to monitor a contrast agent concentration during a contrast scan.

In one aspect of the present disclosure, the target region-of-interest segmentation unit includes a cascaded coarse segmentation unit and fine segmentation unit, where the coarse segmentation unit segments the monitoring slice image to obtain an initial region of interest, and the fine segmentation unit further segments the initial region of interest on the basis of the initial region of interest to obtain the target region of interest.

In one aspect of the present disclosure, the coarse segmentation unit performs coarse segmentation on the monitoring slice image by using at least one of a threshold method, an edge detection method, an erosion expansion method, a region growth method, a level set, or deep learning method. The fine segmentation unit performs fine segmentation on the monitoring slice image by using at least one of a morphological method, a threshold method, an edge detection method, an erosion expansion method, a region growing method, a level set, or deep learning method.

An embodiment of the present application further provides an imaging method, which includes acquiring a positioning image of a scanning object, acquiring a monitoring slice image by determining a key point corresponding to the position of a target region of interest in the positioning image by using a neural network and acquiring the monitoring slice image of the scanning object at the position of the key point, and segmenting the monitoring slice image to obtain the target region of interest.

In one aspect of the present disclosure, the neural network includes a residual neural network.

In one aspect of the present disclosure, the target region of interest is used to monitor a contrast agent concentration during a contrast scan.

In one aspect of the present disclosure, the segmentation of the monitoring slice image to obtain the target region of interest includes performing cascaded coarse segmentation and fine segmentation on the monitoring slice image, where the coarse segmentation segments the monitoring slice image to obtain an initial region of interest, and the fine segmentation further segments the monitoring slice image to obtain the target region of interest.

In one aspect of the present disclosure, the coarse segmentation includes performing segmentation on the slice image by using at least one of a threshold method, an edge detection method, an erosion expansion method, a region growth method, a level set, or deep learning method to obtain the initial region of interest. The fine segmentation includes performing fine segmentation on the monitoring slice image by using at least one of a threshold method, an edge detection method, an erosion expansion method, a region growing method, a level set, or a deep learning method to obtain the target region of interest.

One aspect of the present disclosure further provides a system, including a processor for performing the imaging method according to any one of the foregoing aspects.

One aspect of the present disclosure further provides a computer-readable storage medium storing a computer program thereon, where the program, when executed by a processor, implements the imaging method according to any one of the foregoing aspects.

In the present disclosure, the key point corresponding to the position of the target region of interest in the positioning image can be accurately determined by using the neural network, and further the monitoring slice can be accurately acquired. In addition, the target region of interest can be accurately obtained through segmentation by the cascaded coarse segmentation and fine segmentation. The present disclosure makes it possible to automatically obtain a target region of interest through segmentation by a computer in an imaging process, such that manual operations of an imaging technician are not required.

It should be understood that the brief description above is provided to introduce in a simplified form the technical solutions that will be further described in the detailed description. It is not intended that the brief description above defines the key or essential features claimed of the present disclosure, the scope of which is defined exclusively by the claims. Furthermore, the claimed subject matter is not limited to implementations that solve any disadvantages noted above or in any section of the present disclosure.

These and other features and aspects of the present disclosure will become clearer through the detailed description with reference to the drawings hereinbelow.

BRIEF DESCRIPTION OF THE DRAWINGS

The accompanying drawings included in the present application are intended to help to further understand embodiments of the present application, constitute a part of the specification, and are used to illustrate implementations of the present application and set forth the principles of the present application together with textual description. Obviously, the accompanying drawings in the following description are merely some embodiments of the present application, and a person of ordinary skill in the art could obtain other implementations according to the accompanying drawings without the exercise of inventive effort. In the accompanying drawings.

Figure 1:
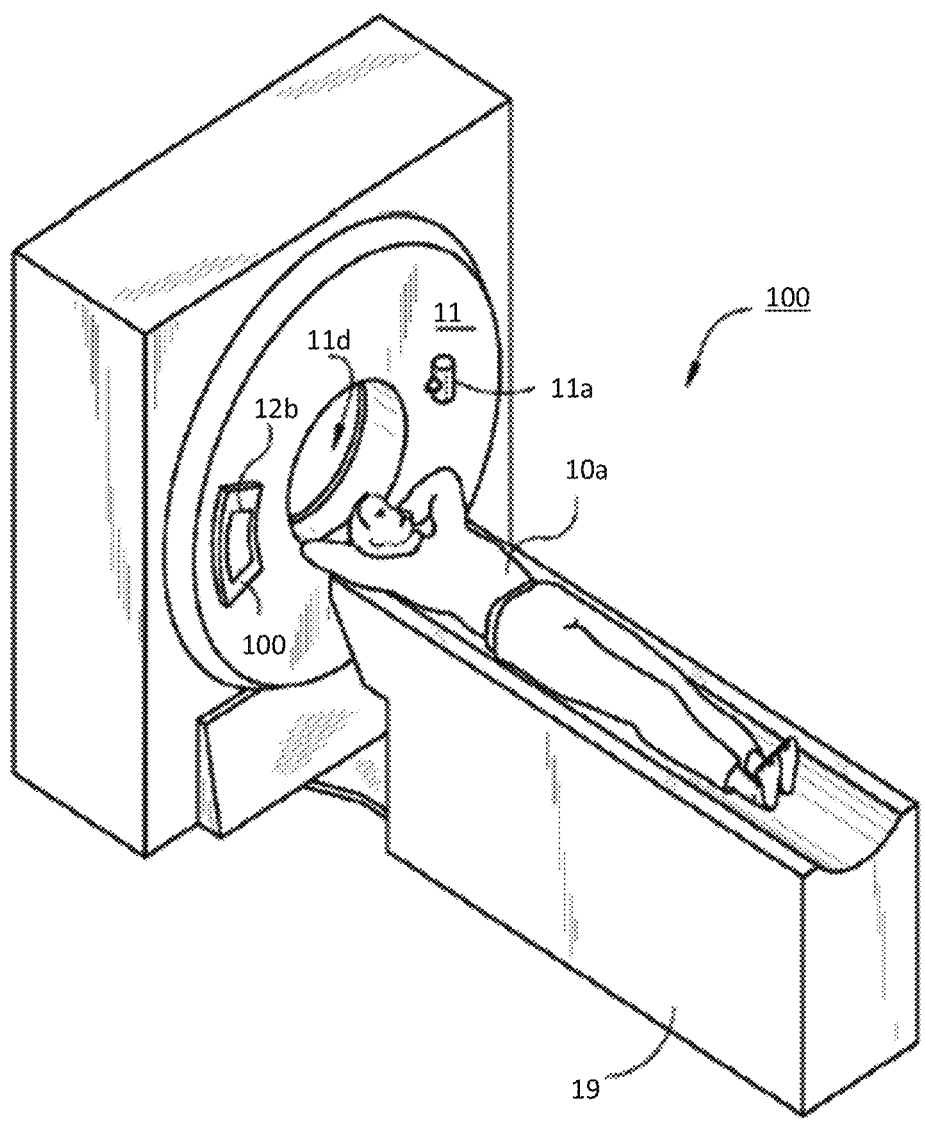
FIG. 1 shows a perspective view of a CT imaging system according to an embodiment of the present disclosure.

It can be expected that the elements in one embodiment of the present disclosure may be advantageously applied to the other embodiments without further elaboration.

DETAILED DESCRIPTION

Specific implementations of the present disclosure will be described below. It should be noted that in the specific description of these embodiments, for the sake of brevity and conciseness, this specification may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Moreover, it can also be understood that although the efforts made in such development process may be complex and lengthy, for those of ordinary skill in the art related to content disclosed in the present disclosure, some changes in design, manufacturing, production or the like based on the technical content disclosed in the present disclosure are only conventional technical means. The content of the present disclosure should not be construed as insufficient.

Unless defined otherwise, technical terms or scientific terms used in the claims and specification should have usual meanings understood by those of ordinary skill in the technical field to which the present disclosure belongs. The terms "first," "second," and similar terms used in the description and claims of the patent application of the present disclosure do not denote any order, quantity, or importance, but are merely intended to distinguish between different constituents. The terms "one" or "a/an" and similar terms do not denote a limitation of quantity, but rather the presence of at least one. The terms "include" or "comprise" and similar terms mean that an element or article in front of "include" or "comprise" encompass elements or articles and their equivalent elements listed after "include" or "comprise", and do not exclude other elements or articles. The term "connect" or "connected" and similar words are not limited to physical or mechanical connections, and are not limited to direct or indirect connections.

The imaging system and method described herein may be applicable to various medical imaging modalities, including but not limited to, computed tomography (CT) apparatuses, magnetic resonance imaging (MRI) apparatuses, C-arm imaging apparatuses, or any other suitable medical imaging apparatuses. The imaging system may include the aforementioned medical imaging apparatus, and may include a separate computer apparatus connected to the medical imaging apparatus, and may further include a computer apparatus connected to an Internet cloud. The computer apparatus is connected via the Internet to the medical imaging apparatus or a memory for storing medical images. The imaging method may be independently or jointly implemented by the aforementioned medical imaging apparatus, the computer apparatus connected to the medical imaging apparatus, and the computer apparatus connected to the Internet cloud.

As an example, the present disclosure is described below in conjunction with an X-ray computed tomography (CT) apparatus. Those skilled in the art will appreciate that the present disclosure may also be applicable to other medical imaging apparatuses suitable for imaging.

Figure 2:
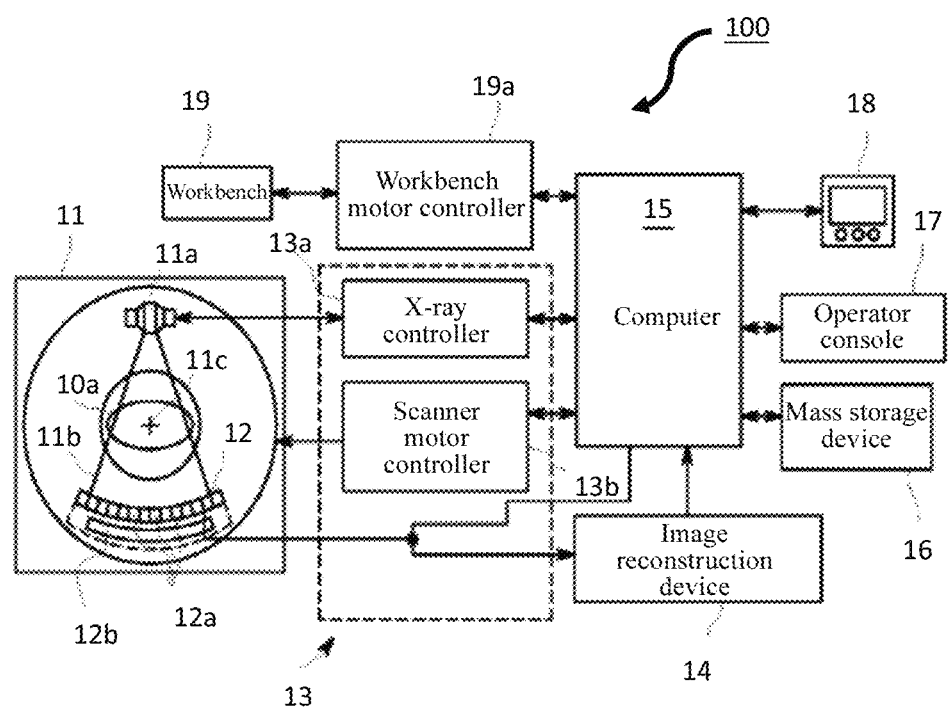
FIG. 2 shows a block diagram of a CT imaging system according to an embodiment of the present disclosure.

FIG. 1 shows a CT imaging apparatus 100 to which imaging systems and methods according to exemplary embodiments of the present disclosure are applicable. FIG. 2 is a schematic block diagram of the example CT imaging system 100 shown in FIG. 1.

Referring to FIG. 1, the CT imaging system 100 is shown as including a scanning gantry 11. The scanning gantry 11 has an X-ray source 11a, and the X-ray source 11a projects an X-ray beam toward a detector assembly or collimator 12 on an opposite side of the scanning gantry 11.

Referring to FIG. 2, the detector assembly 12 includes a plurality of detector units 12a and a data acquisition system (DAS) 12b. The plurality of detector units 12a sense the projected X-rays 11b passing through an object 10.

The DAS 12b converts, according to the sensing of the detector units 12a, collected information into projection data for subsequent processing. During the scanning for acquiring the X-ray projection data, the scanning gantry 11 and components mounted thereon rotate around a rotation center 11c.

The rotation of the scanning gantry 11 and the operation of the X-ray source 11a are controlled by a control mechanism 13 of the CT system 100. The control mechanism 13 includes an X-ray controller 13a that provides power and a timing signal to the X-ray source 11a and a scanner motor controller 13b that controls the rotation speed and position of the scanning gantry 11. An image reconstruction device 14 receives the projection data from the DAS 12b and performs image reconstruction. A reconstructed image is transmitted as an input to a computer 15, and the computer 15 stores the image in a mass storage device 16.

The computer 15 also receives commands and scan parameters from an operator through a console 17, and the console 17 has an operator interface in a certain form, such as a keyboard, a mouse, a voice activated controller, or any other suitable input device. An associated display 18 allows the operator to observe the reconstructed image and other data from the computer 15. The commands and parameters provided by the operator are used by the computer 15 to provide control signals and information to the DAS 12b, the X-ray controller 13a, and the scanning gantry motor controller 13b. In addition, the computer 15 operates a workbench motor controller 19a, which controls a workbench 19 so as to position the object 10 and the scanning gantry 11. In particular, the workbench 19 moves the object 10 in whole or in part to pass through a scanning gantry opening 11d in FIG. 1.

Figure 3:
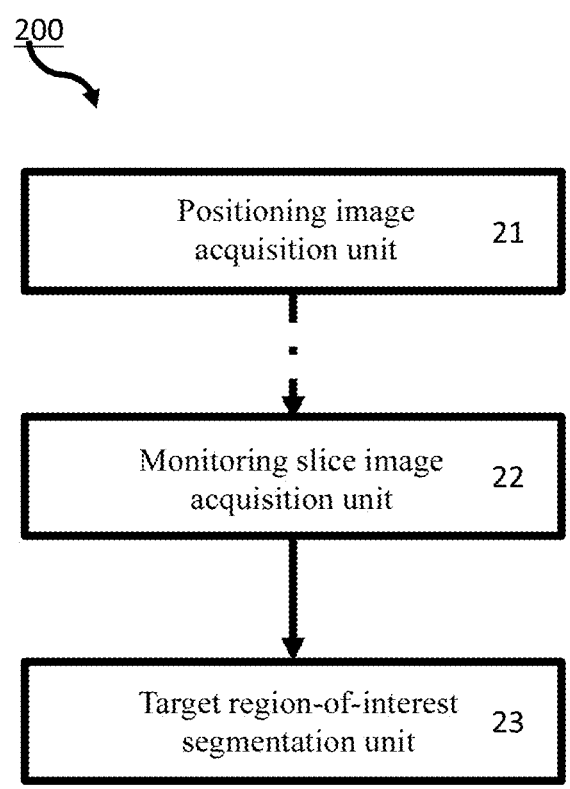
FIG. 3 shows a block diagram of an imaging system according to an embodiment of the present disclosure.

FIG. 3 shows an example block diagram of an imaging system 200 according to an embodiment of the present disclosure. The imaging system 200 includes a positioning image acquisition unit 21, a monitoring slice image acquisition unit 22, and a target region-of-interest segmentation unit 23. For example, these units 21, 22, 23 may be implemented as part of or executed by the computer 15 of the CT imaging system 100 shown in FIG. 1 and FIG. 2. The positioning image acquisition unit 21 is configured to acquire a positioning image of a scanning object. The monitoring slice image acquisition unit 22 is configured to determine a key point corresponding to the position of a target region of interest in the positioning image by using a neural network, and acquire a slice image of the scanning object at the position of the key point. The target region-of-interest segmentation unit 23 is configured to segment the monitoring slice image to obtain the target region of interest.

The positioning image acquisition unit 21 is configured to acquire the positioning image of the scanning object. For example, in CT scan imaging, a positioning scan is usually performed before a formal scan. That is, an X-ray tube in a scanning gantry is kept fixed at a preset position during the positioning scan, a scanning bed moves in parallel in a scanning direction or a z-direction during exposure, and at the same time, the X-ray tube emits low-dose X-rays to the scanning object, and a CT scanner reconstructs a plane positioning image according to signals detected by a detector. The positioning image obtained from the positioning scan contains a part of interest of the scanning object. The positioning image may be used to set appropriate scanning parameters for a subsequent formal scan of the part of interest, such as a scanning start position and a scanning end position, an angle, a layer thickness, etc. of the part to be scanned. For example, the part of interest may include the lungs, heart, abdomen, pelvis, etc. For example, the positioning image may be a forward positioning image or a lateral positioning image.

Figure 4:
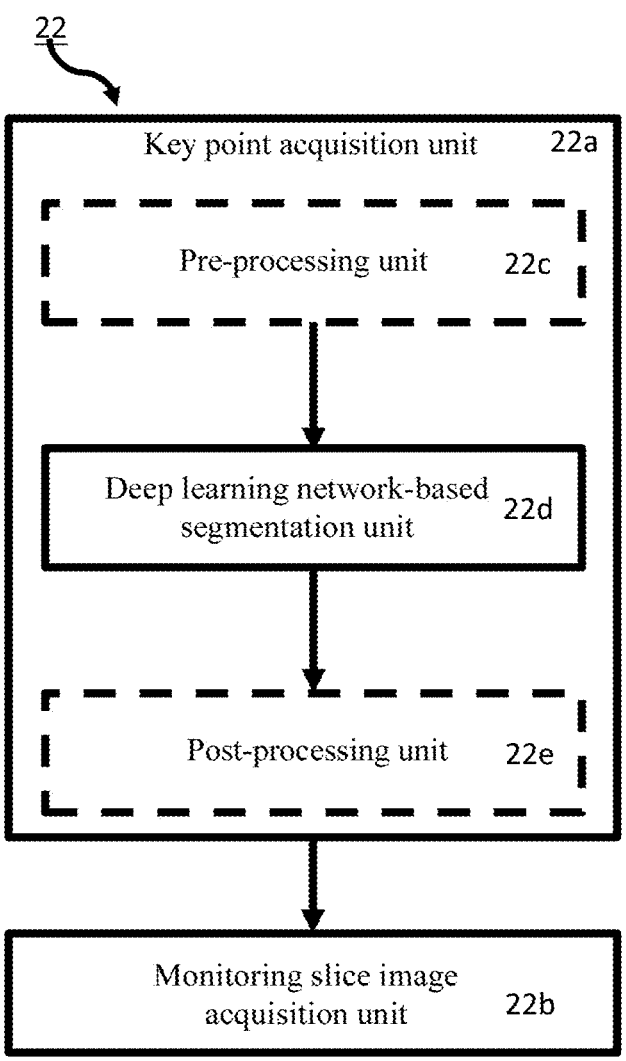
FIG. 4 shows a block diagram of a monitoring slice image acquisition unit according to an embodiment of the present disclosure.
Figure 5:
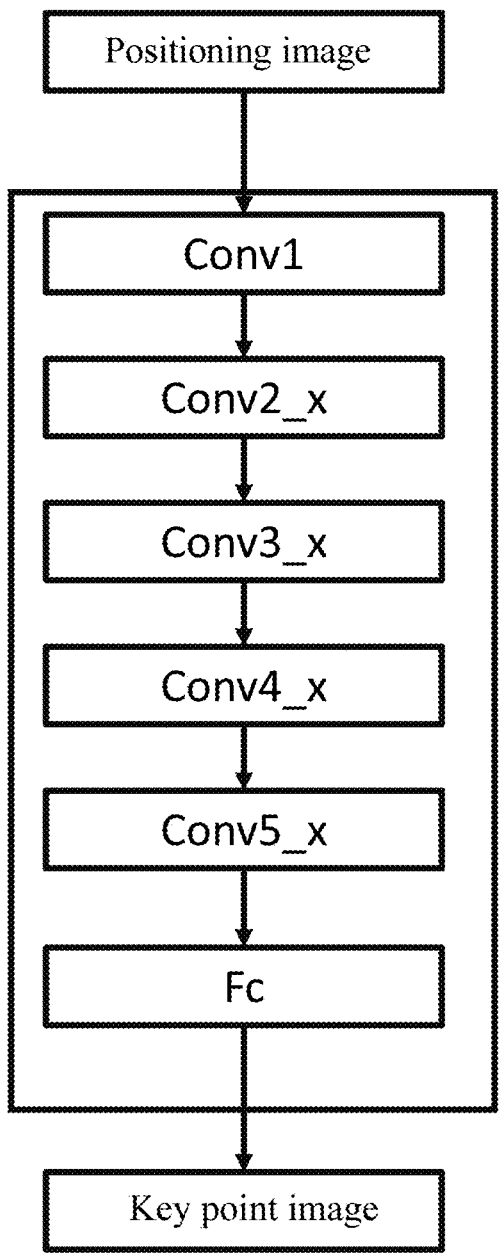
FIG. 5 shows a block diagram of a deep learning network-based segmentation unit according to an embodiment of the present disclosure.

The monitoring slice image acquisition unit 22 is configured to determine the key point corresponding to the position of the target region of interest in the positioning image by using a neural network, and acquire the slice image of the scanning object at the position of the key point. FIG. 4 shows the monitoring slice image acquisition unit 22 according to an embodiment of the present disclosure, which includes a key point acquisition unit 22a and a monitoring slice image acquisition unit 22b, where the key point acquisition unit 22a determines the key point corresponding to the position of the target region of interest in the positioning image by using a neural network, and the monitoring slice image acquisition unit 22b acquires the slice image of the scanning object at the position of the key point.

As also shown in FIG. 4, the key point acquisition unit 22a includes a pre-processing unit 22c, a deep learning network-based segmentation unit 22d, and a post-processing unit 22e. The pre-processing unit 22c is configured to pre-process the aforementioned positioning image. For example, the pre-processing may include any one or more of window width/window level adjustment, normalization, image scaling, image cropping, or image flipping on the positioning image. For example, the window width/window level adjustment can adjust the window width/window level value of the positioning image according to characteristics of the part of interest, for example, adjusting the window width/window level value of the lung thoracic diaphragm to 150/450, and the window width/window level value of other parts to 250/450. It can be understood that the pre-processing unit 22c can optimize the positioning image to facilitate subsequent key point segmentation by the deep learning network-based segmentation unit 22d, but the pre-processing unit 22c is not necessary, and is represented by a dotted block in FIG. 3.

The deep learning network-based segmentation unit 22d is configured to further process the positioning image processed by the pre-processing unit 22c to obtain the key point corresponding to the target region of interest through segmentation. The key point is located on the monitoring slice image and corresponds to the position of the target region of interest, and the target region of interest may be used to monitor a contrast agent concentration in an organ of interest during a contrast scan. For example, the bronchial carina may be selected as a key point of the lung, a position one centimeter below the bronchial carina may be selected as a key point of the heart, the upper edge of the diaphragm may be selected as a key point of the abdomen, and the upper edge of the iliac crest may be selected as a key point of the pelvis.

As shown in FIG. 4, for example, the deep learning network-based segmentation unit 22d may use a residual network (ResNet), which includes five convolutional layer parts conv1, conv2_x, conv3_x, conv4_x, and conv5_x and a fully connected layer Fc. The residual network may employ an 18-layer, 34-layer, 50-layer, 101-layer, or 152-layer network structure. The positioning image is input to the trained residual network, and after segmentation by the residual network, a key point image is output. For example, the key point image may be a feature heat map.

The post-processing unit 22e may further process the feature heat map of the key point obtained by the deep learning network-based segmentation unit 22d through segmentation. It can be understood that the post-processing unit 22e is not necessary, and is represented by a dotted block in FIG. 4.

The monitoring slice image acquisition unit 22b performs axial scanning according to the position of the key point to obtain the monitoring slice image.

Figure 6A:
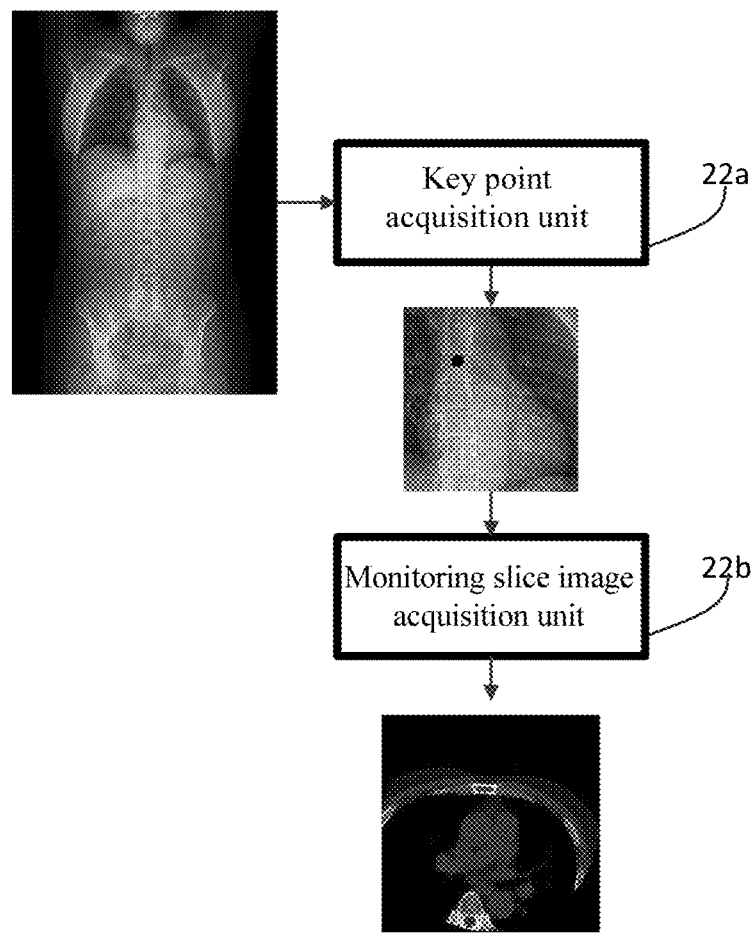
FIG. 6a to FIG. 6c show block diagrams of a monitoring slice image acquisition unit acquiring a monitoring slice image of a specific part according to an embodiment of the present disclosure.
Figure 6B:
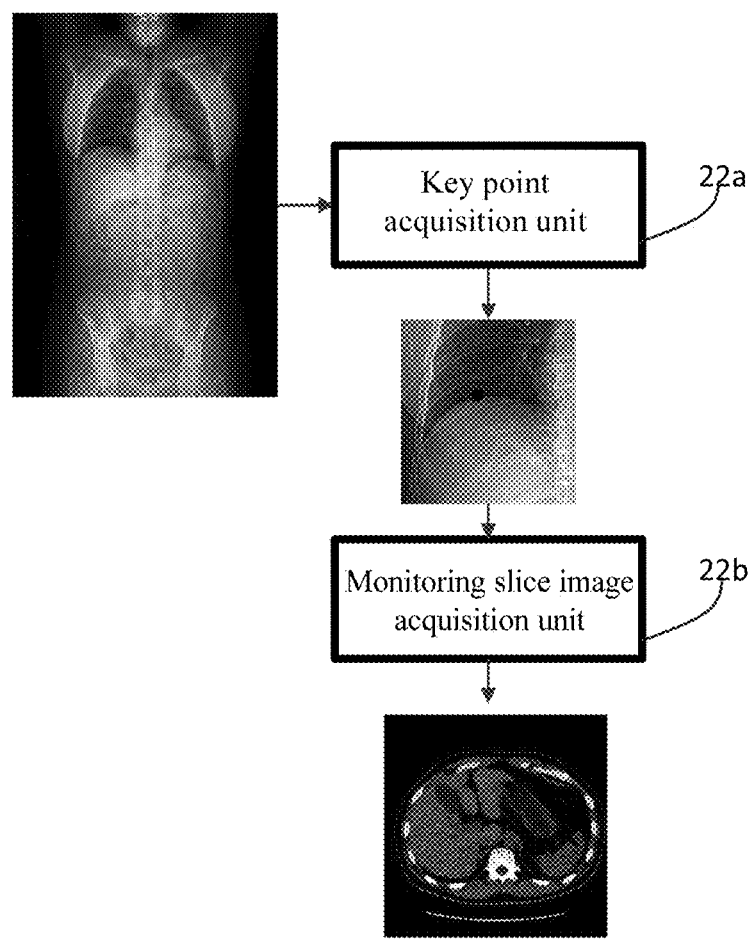
Figure 6C:
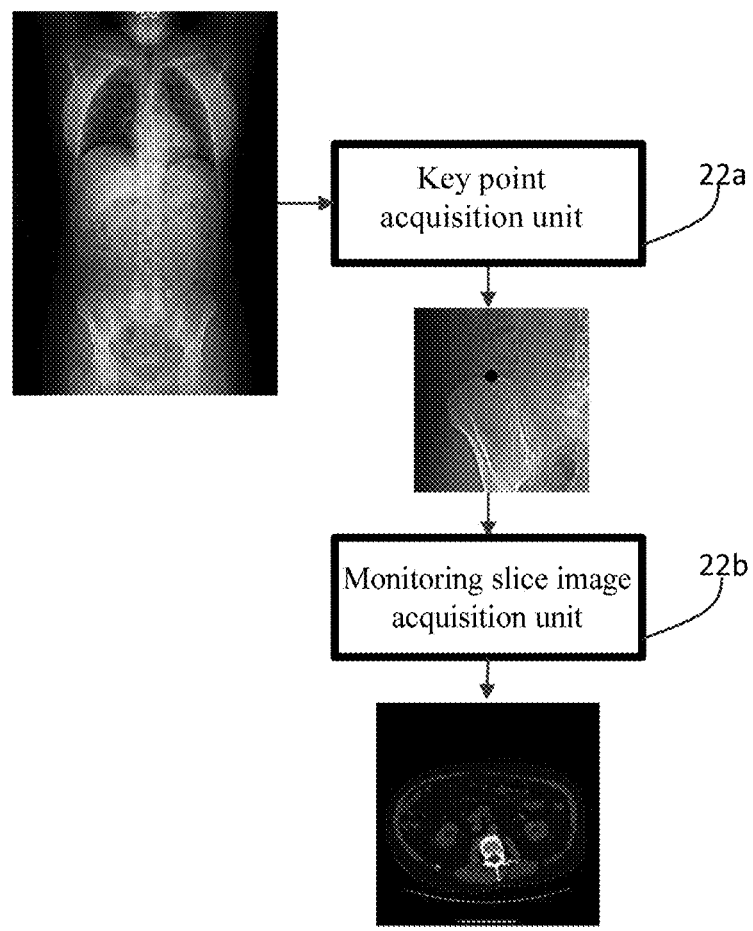

FIG. 6a to FIG. 6c show the monitoring slice image of the part of interest obtained by the monitoring slice image acquisition unit 22 according to the present application. FIG. 6a shows the acquisition of a monitoring slice image of a heart part. The positioning image is input to the key point acquisition unit 22a, and the key point acquisition unit 22a obtains a key point of the heart part by using the deep learning network 22d through segmentation. For example, the key point may be a position one centimeter below the bronchial carina. The monitoring slice image acquisition unit 22b acquires a slice image at the position of the key point after the imaging system scans the heart part, and the slice image is a monitoring slice image of the heart part.

FIG. 6b shows the acquisition of a monitoring slice image of an abdominal part. The positioning image is input to the key point acquisition unit 22a, and the key point acquisition unit 22a obtains a key point of the abdominal part by using the deep learning network 22d through segmentation. For example, the key point may be the upper edge of the diaphragm. The monitoring slice image acquisition unit 22b acquires a slice image at the position of the key point after the imaging system scans the abdominal part, and the slice image is a monitoring slice image of the abdominal part.

FIG. 6c shows the acquisition of a monitoring slice image of a pelvic part. The positioning image is input to the key point acquisition unit 22a, and the key point acquisition unit 22a obtains a key point of the pelvic part by using the deep learning network 22d through segmentation. For example, the key point may be the upper edge of the iliac crest. The monitoring slice image acquisition unit 22b acquires a slice image at the position of the key point after the imaging system scans the pelvic part, and the slice image is a monitoring slice image of the pelvic part.

It can be understood that the positions of the same region of interest in different scanning objects are different. By determining the key point, the position of the target region of interest in the scanning object can be more accurately reflected. In the imaging system according to the present embodiment, by using the neural network, the key point corresponding to the position of the target region of interest in the positioning image can be accurately determined, and further the monitoring slice image can be accurately acquired.

Figure 7:
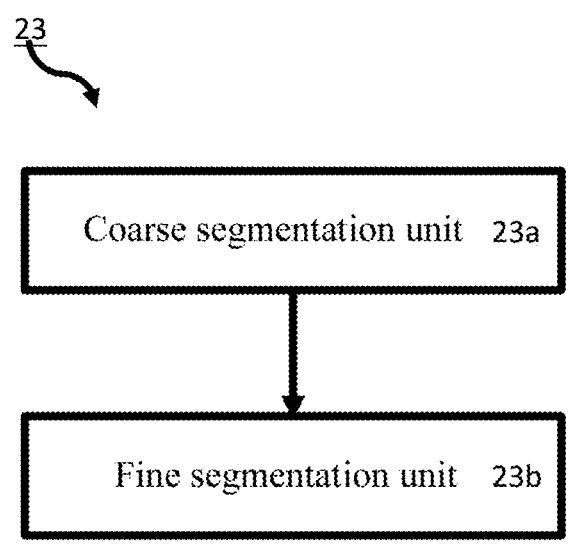
FIG. 7 shows a block diagram of a target region-of-interest segmentation unit of an imaging system according to an embodiment of the present disclosure.

FIG. 7 shows the target region-of-interest segmentation unit 23 according to an embodiment of the present application. The target region-of-interest segmentation unit 23 segments the aforementioned monitoring slice image to obtain the target region of interest, and the target region of interest can be used to monitor the flow rate of a contrast agent during a contrast scan to trigger a diagnostic scan. The target region-of-interest segmentation unit 23 includes a cascaded coarse segmentation unit 23a and fine segmentation unit 23b.

The coarse segmentation unit 23a can segment the monitoring slice image to obtain an initial region of interest. The initial region of interest is larger than the target region of interest (that is, the initial region of interest includes not only the target region of interest, but also includes regions around the target region of interest), or the initial region of interest may have relatively blurred boundaries, or the initial region of interest has less tissue structure detail information. The coarse segmentation unit 23a may employ at least one of a threshold method, an edge detection method, an erosion expansion method, a region growth method, a level set method, or deep learning method. For example, the coarse segmentation unit 23a may coarsely segment the monitoring slice image by using a U-net neural network, and optionally, may pre-process the monitoring slice image before the coarse segmentation, such as performing adjustment of a window width/window level value, normalization, rotation according to the angle of the scanning object, etc. Optionally, after the coarse segmentation is performed by using the U-net neural network, post-processing may also be performed on the obtained initial region of interest, to facilitate subsequent fine segmentation on the image by the fine segmentation unit 23b.

The fine segmentation unit 23b can perform further segmentation on the basis of the initial normalized region of interest resulting from segmentation to obtain the target region of interest. The target region of interest may have clearer boundaries and more tissue structure detail information. The fine segmentation unit 23b may employ at least one of a morphological method, a threshold method, an edge detection method, an erosion expansion method, a region growth method, a level set method, or deep learning method.

In the target region-of-interest segmentation unit 23, the fine segmentation unit 23b can obtain a relatively clear region of interest through segmentation, especially for small tissues.

Figure 8:
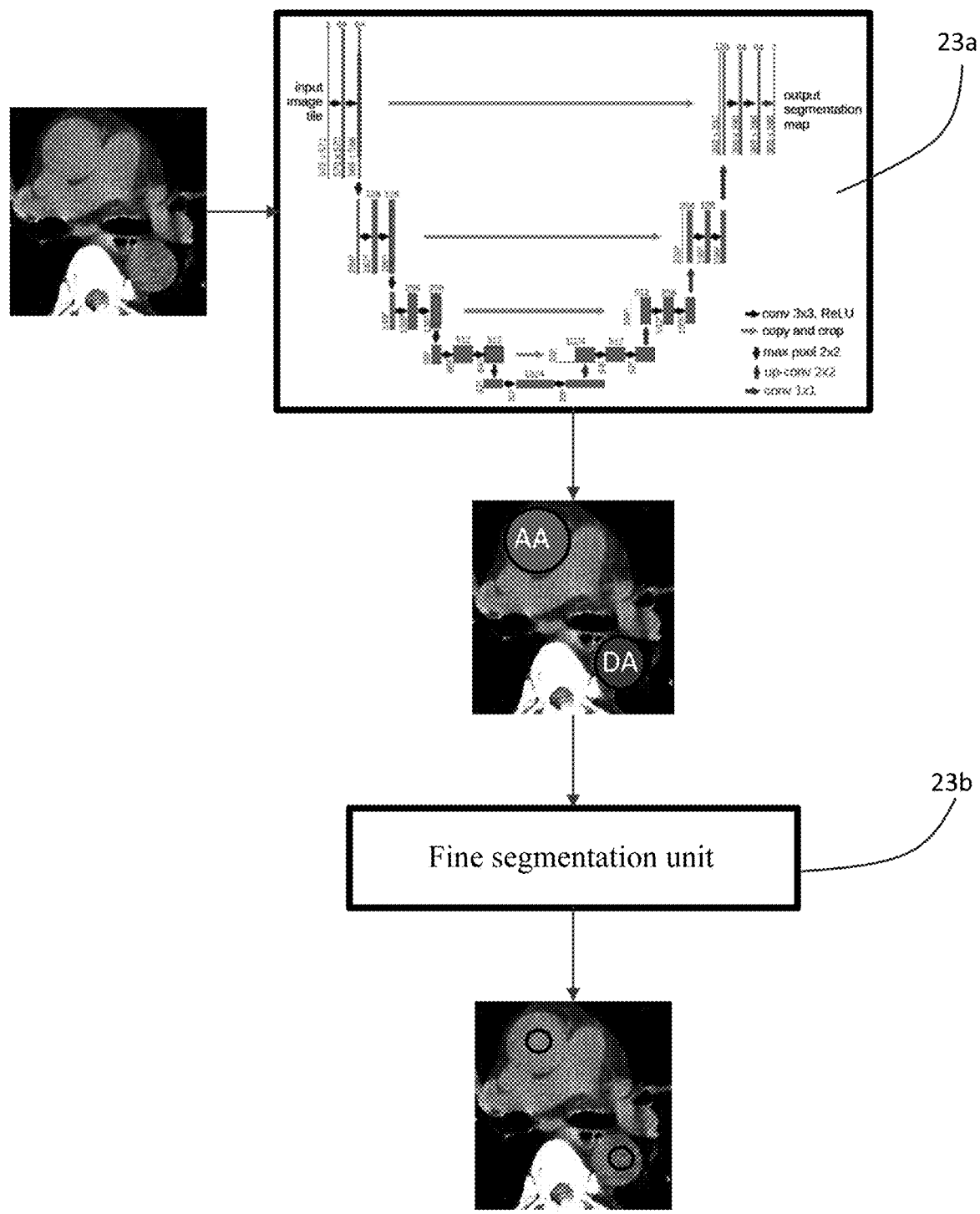
FIG. 8 shows a block diagram of a target region-of-interest segmentation unit obtaining a target region of interest of a specific part through segmentation according to an embodiment of the present disclosure.

FIG. 8 shows an example of segmenting a lung monitoring slice image by the target region-of-interest segmentation unit 23 according to the embodiment, wherein the coarse segmentation unit 23a uses a U-Net neural network to coarsely segment the lung monitoring slice image. It can be seen that an ascending aorta (AA) and a descending aorta (DA) as initial regions of interest have comparatively large areas. After further segmentation by the fine segmentation unit 23b, the areas of the ascending aorta (AA) and the descending aorta (DA) as the target regions of interest are reduced, and the target regions of interest can more accurately reflect the flow rate of a contrast agent during contrast imaging.

It can be understood that the target region-of-interest segmentation unit 23 can be used not only to segment the lung monitoring slice image to obtain the target region of interest, but also to perform segmentation to obtain target regions of interest in a heart part, an abdominal part, a pelvic part, etc.

It can be understood that, according to the embodiment of the present application, the coarse segmentation can obtain the initial region of interest including the target region of interest through segmentation, and then fine segmentation is performed on the initial region of interest as a data set to be processed. The initial region of interest has a smaller area, a smaller amount of data, and less image information relative to the original monitoring image, and can better reflect the target region of interest. Therefore, the region of interest can be more accurately obtained through segmentation through subsequent fine segmentation. In addition, the present disclosure can automatically perform segmentation to obtain the target region of interest by means of a computer during the imaging process, such that manual operations of an imaging technician are not required.

Figure 9:
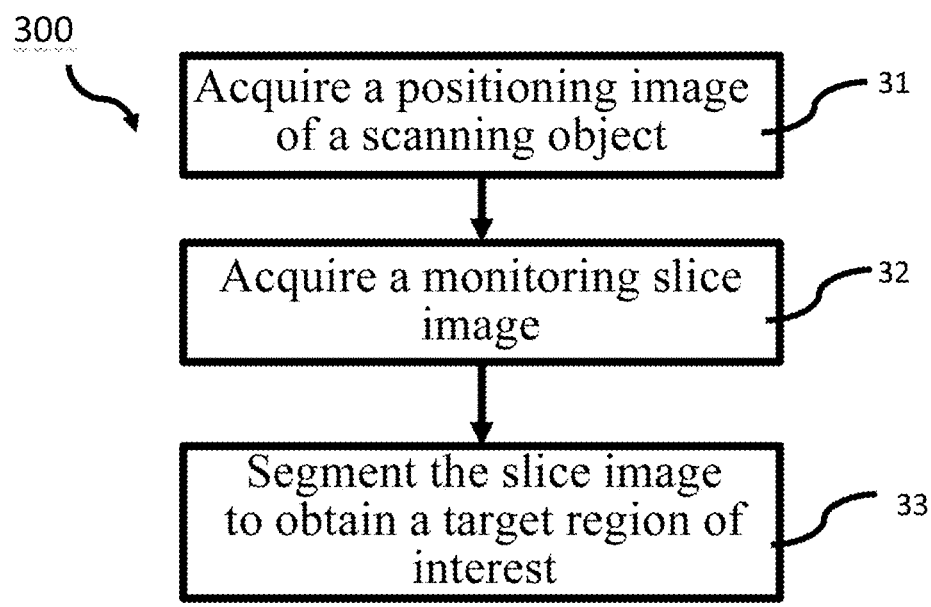
FIG. 9 shows a flowchart block diagram of an imaging method according to an embodiment of the present disclosure.

FIG. 9 shows an example block diagram of an imaging method according to an embodiment of the present disclosure. The imaging method 300 includes acquiring a positioning image of a scanning object 31, acquiring a slice image 32, and segmenting the slice image to obtain a target region of interest 33. For example, the imaging method 300 may be performed by the computer 15 of the CT imaging system 100 shown in FIG. 1 and FIG. 2.

In step 31, the positioning image of the scanning object is acquired. For example, in CT scan imaging, a positioning scan is usually performed before a formal scan, to obtain the positioning image of the scanning object.

Figure 10:
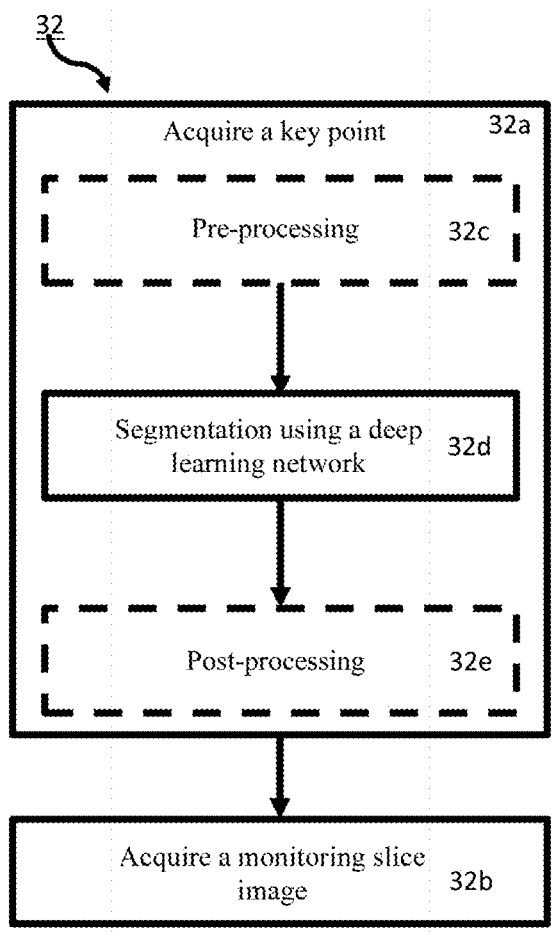
FIG. 10 shows a flowchart block diagram of an imaging method used to acquire a monitoring slice image according to an embodiment of the present disclosure.

In step 32, the monitoring slice image is acquired by determining a key point corresponding to the position of a target region of interest in the positioning image by using a neural network, and acquiring the slice image of the scanning object at the position of the key point. As shown in FIG. 10, for example, acquiring the slice image 32 includes acquiring the key point 32a and acquiring the slice image 32b, where acquiring the key point 32a includes determining the key point corresponding to the position of the target region of interest in the positioning image by using a neural network, and acquiring the slice image 32b includes acquiring the slice image of the scanning object at the position of the key point.

Acquiring the key point 32a includes pre-processing 32c, deep learning network-based segmentation 32d, and post-processing 32e. The pre-processing 32c may include any one or more of window width/level adjustment, normalization, image scaling, image cropping, or image flipping on the positioning image. For example, the window width/window level adjustment can adjust the window width/window level value of the positioning image according to characteristics of the part of interest, for example, adjusting the window width/window level value of the lung thoracic diaphragm to 150/450, and the window width/window level value of other parts to 250/450. It can be understood that the pre-processing 32c can optimize the positioning image to facilitate subsequent key point segmentation in the deep learning network-based segmentation 32d, but the pre-processing 32c is not necessary, and is represented by a dotted block in FIG. 10.

The deep learning network-based segmentation 32d is used to further process the preprocessed positioning image to obtain the key point corresponding to the target region of interest through segmentation. The key point can represent to some extent a contrast agent concentration in an organ of interest during a contrast scan. For example, the bronchial carina may be selected as a key point of the lung, a position one centimeter below the bronchial carina may be selected as a key point of the heart, the upper edge of the diaphragm may be selected as a key point of the abdomen, and the upper edge of the iliac crest may be selected as a key point of the pelvis. For example, the deep learning network-based segmentation 32d can use a residual network (ResNet) to segment the positioning image, i.e., inputting the positioning image to a trained residual network, and outputting a key point image after segmentation by the residual network. For example, the key point image may be a feature heat map.

For example, the post-processing 32e may further process the feature heat map of the key point acquired through the deep learning network-based segmentation. It can be understood that the post-processing 32e is not necessary, and is represented by a dotted block in FIG. 10.

The slice image acquisition 32b may include performing axial scanning according to the position of the key point to obtain the monitoring slice image.

Figure 11:
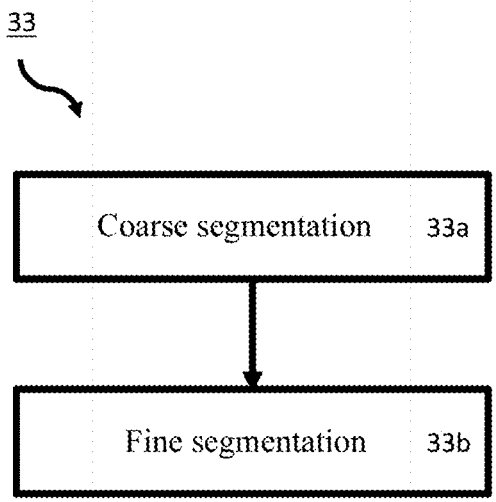
FIG. 11 shows a flowchart block diagram of an imaging method used to obtain a target region of interest through segmentation according to an embodiment of the present disclosure.

FIG. 11 shows the target region-of-interest segmentation 33 according to an embodiment of the present application. The region-of-interest segmentation 33 includes segmenting the aforementioned monitoring slice image to obtain the target region of interest, and the target region of interest can be used to monitor the flow rate of a contrast agent during a contrast scan to trigger a diagnostic scan. The target region-of-interest segmentation 33 includes cascaded coarse segmentation 33a and fine segmentation 33b.

The coarse segmentation 33a can segment the monitoring slice image to obtain an initial region of interest. The initial region of interest is larger than the target region of interest (that is, the initial region of interest includes not only the target region of interest, but also includes regions around the target region of interest), or the initial region of interest may have relatively blurred boundaries, or the initial region of interest has less tissue structure detail information. The coarse segmentation 33a may employ at least one of a threshold method, an edge detection method, an erosion expansion method, a region growth method, a level set method, or deep learning method. For example, the coarse segmentation 33a may coarsely segment the monitoring slice image by using a U-net neural network, and optionally, may pre-process the monitoring slice image before the coarse segmentation, such as performing adjustment of a window width/window level value, normalization, rotation according to the angle of the scanning object, etc. Optionally, after the coarse segmentation is performed by using the U-net neural network, post-processing may also be performed on the obtained initial region of interest, to facilitate subsequent fine segmentation on the image in the fine segmentation 33b.

The fine segmentation 33b can perform further segmentation on the basis of the initial normalized region of interest resulting from segmentation to obtain the target region of interest. The target region of interest may have clearer boundaries and more tissue structure detail information. The fine segmentation 33b may employ at least one of a morphological method, a threshold method, an edge detection method, an erosion expansion method, a region growth method, a level set method, or deep learning method.

It can be understood that according to this embodiment of the present application, the acquisition of the positioning image of the scanning object 31, the acquisition of the slice image 32, and the segmentation of the slice image to obtain the target region of interest 33 in the imaging method can be automatically performed by a computer, without the need for manual operations of an imaging technician.

Figure 12:
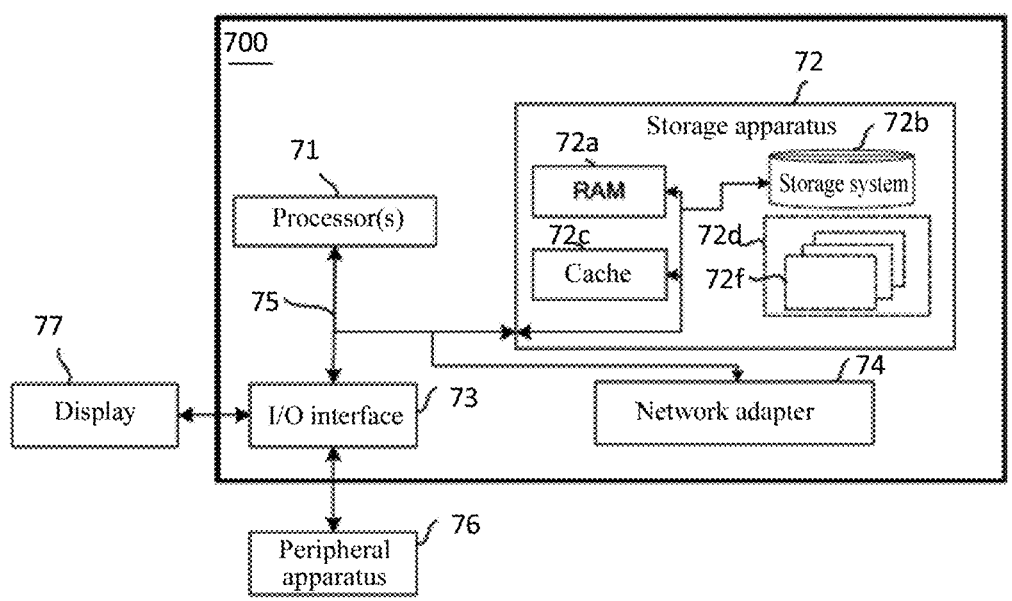
FIG. 12 shows an example of an electronic apparatus that performs an imaging method according to an embodiment of the present disclosure.

FIG. 12 shows an example of an electronic apparatus 700 that performs an imaging method according to an embodiment of the present disclosure. The electronic apparatus 700 includes: one or a plurality of processors 71; and a storage device 72, configured to store one or a plurality of programs, where when the one or plurality of programs are executed by the one or plurality of processors 71, the one or plurality of processors 71 are caused to implement the imaging method described herein. The processor is, for example, a digital signal processor (DSP), a microcontroller, an application-specific integrated circuit (ASIC), or a microprocessor.

The electronic apparatus 700 shown in FIG. 12 is only an example, and should not bring any limitation to the function and application scope of the embodiment of the present disclosure.

As shown in FIG. 12, the electronic apparatus 700 is represented in the form of a general-purpose computing device. The components of the electronic apparatus 700 may include, but are not limited to, one or a plurality of processors 71, a storage device 72, and a bus 75 connecting different system components (including the storage device 72 and the processor 71).

The bus 75 represents one or a plurality of types of bus structures, including a memory bus or a memory controller, a peripheral bus, an accelerated graphics port, a processor, or a local bus using any bus structure in the plurality of bus structures. For example, these architectures include, but are not limited to, an Industrial Standard Architecture (ISA) bus, a Micro Channel Architecture (MAC) bus, an enhanced ISA bus, a Video Electronics Standards Association (VESA) local bus, and a Peripheral Component Interconnect (PCI) bus.

The electronic apparatus 700 typically includes a variety of computer system readable media. These media may be any available medium that can be accessed by the electronic apparatus 700, including volatile and non-volatile media as well as removable and non-removable media.

The storage apparatus 72 may include a computer system readable medium in the form of a volatile memory, for example, a random access memory (RAM) 72a and/or a cache memory 72c. The electronic apparatus 700 may further include other removable/non-removable, and volatile/non-volatile computer system storage media. Only as an example, a storage system 72b may be configured to read/write a non-removable, non-volatile magnetic medium (not shown in FIG. 12, often referred to as a "hard disk drive"). Although not shown in FIG. 12, a magnetic disk drive configured to read/write a removable non-volatile magnetic disk (for example, a "floppy disk") and an optical disc drive configured to read/write a removable non-volatile optical disc (for example, a CD-ROM, a DVD-ROM, or other optical media) may be provided. In these cases, each drive may be connected to the bus 75 via one or a plurality of data medium interfaces. The storage device 72 may include at least one program product which has a group of program modules (for example, at least one program module) configured to perform the functions of the embodiments of the present disclosure.

A program/utility tool 72d having a group (at least one) of program modules 72f may be stored in, for example, the storage apparatus 72. Such a program module 72f includes, but is not limited to, an operating system, one or a plurality of application programs, other program modules, and program data, and each of these examples or a certain combination thereof may include the implementation of a network environment. The program module 72f typically performs the function and/or method in any embodiment described in the present disclosure.

The electronic apparatus 700 may also communicate with one or a plurality of peripheral devices 76 (such as a keyboard, a pointing device, and a display 77), and may further communicate with one or a plurality of devices that enable a user to interact with the electronic apparatus 700, and/or communicate with any device (such as a network card and a modem) that enables the electronic apparatus 700 to communicate with one or a plurality of other computing devices. Such communication may be carried out via an input/output (I/O) interface 73. In addition, the electronic apparatus 700 may also communicate with one or a plurality of networks (for example, a local area network (LAN), a wide area network (WAN), and/or a public network, such as the Internet) via a network adapter 74. As shown in FIG. 12, the network adapter 74 communicates with other modules of the electronic apparatus 700 through the bus 75. It should be understood that although not shown in the drawing, other hardware and/or software modules, including, but not limited to: microcode, device drivers, redundant processing units, external disk drive arrays, RAID systems, tape drives, data backup storage system, and the like may be used in conjunction with the electronic apparatus 700.

The processor 71 executes various functional applications and data processing by running programs stored in the storage apparatus 72.

According to an embodiment of the present disclosure, a computer readable medium is further provided. The computer readable medium has instructions thereon, and when executed by a processor, the instructions cause the processor to perform the steps of the method of the present disclosure. The computer-readable medium may include, but is not limited to, a non-transitory, tangible arrangement of an article manufactured or formed by a machine or apparatus, including a storage medium such as the following: a hard disk; any other type of disk including a floppy disk, an optical disk, a compact disk read-only memory (CD-ROM), a compact disk rewritable (CD-RW), and a magneto-optical disk; a semiconductor device such as a read-only memory (ROM), a random access memory (RAM) such as a dynamic random access memory (DRAM) and a static random access memory (SRAM), an erasable programmable read-only memory (EPROM), a flash memory, and an electrically erasable programmable read-only memory (EEPROM); a phase change memory (PCM); a magnetic or optical card; or any other type of medium suitable for storing electronic instructions. The computer-readable medium may be installed in a CT device, or may be installed in a separate control device or computer that remotely controls the CT device.

Figure 13:
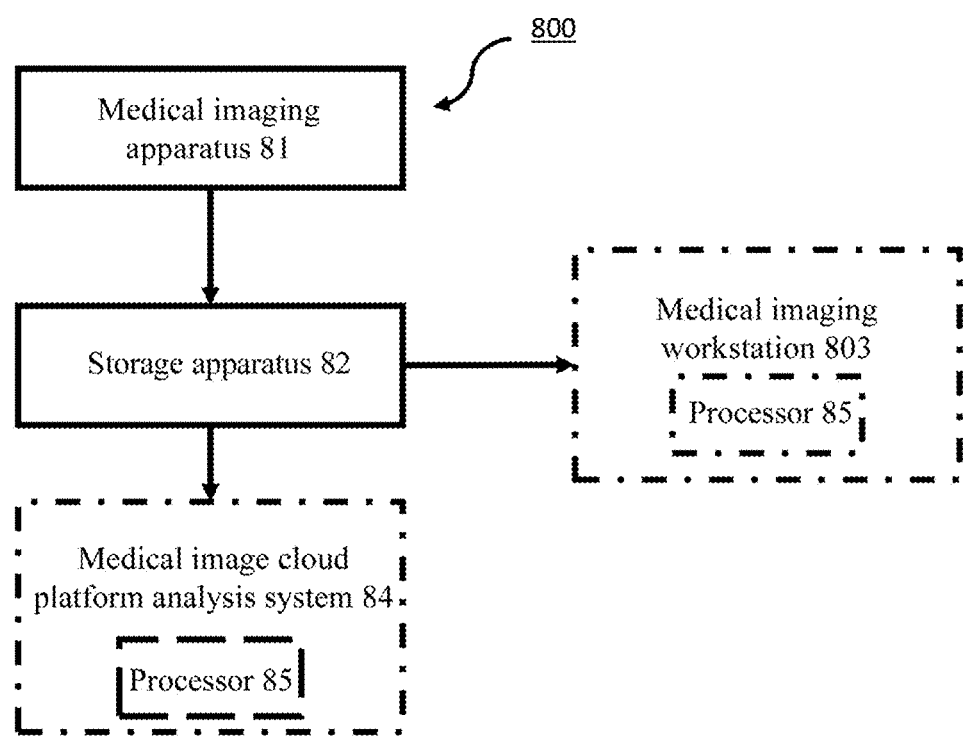
FIG. 13 shows an example of an imaging system that performs an imaging method according to an embodiment of the present disclosure.

FIG. 13 shows a block diagram of an exemplary imaging system 800 according to an embodiment of the present disclosure. Referring to FIG. 13, the imaging system 800 may include a medical imaging apparatus 81 configured to perform imaging scanning to generate a medical image, a storage apparatus 82 configured to store the medical image, and a medical imaging workstation 83 or a medical image cloud platform analysis system 84 communicatively connected to the storage apparatus 82 and including a processor 85. The processor 85 may be configured to perform the foregoing imaging method of the present disclosure.

The medical imaging device 81 may be a CT apparatus, an MRI apparatus, or any other suitable imaging apparatuses. The storage apparatus 82 may be located in the medical imaging apparatus 81, a server external to the medical imaging apparatus 81, an independent medical image storage system (such as a PACS), and/or a remote cloud storage system. The medical imaging workstation 83 may be disposed locally at the medical imaging apparatus 81, that is, the medical imaging workstation 83 being disposed adjacent to the medical imaging apparatus 81, and the two may be co-located in a scanning room, a medical imaging department, or the same hospital. The medical image cloud platform analysis system 84 may be located away from the medical imaging apparatus 81, for example, arranged at the cloud in communication with the medical imaging apparatus 81. As an example, after a medical institution completes an imaging scan using the medical imaging apparatus 81, data obtained by the scanning is stored in the storage apparatus 82. The medical imaging workstation 83 may directly read the data obtained by the scanning, and process the data by using the method of the present disclosure via its processor. As another example, the medical image cloud platform analysis system 84 may read the medical image in the storage apparatus 82 via remote communication to provide "software as a service (SaaS)." SAAS can exist between hospitals, between a hospital and an imaging center, or between a hospital and a third-party online diagnosis and treatment service provider.

The technology described in the present disclosure may be implemented at least in part through hardware, software, firmware, or any combination thereof. For example, aspects of the technology may be implemented through one or more microprocessors, digital signal processors (DSP), application-specific integrated circuits (ASIC), field programmable gate arrays (FPGA), or any other equivalent integrated or separate logic circuits, and any combination of such parts embodied in a programmer (such as a doctor or patient programmer, stimulator, or the other apparatuses). The term "processor", "processing circuit", "controller" or "control module" may generally refer to any of the above noted logic circuits (either alone or in combination with other logic circuits), or any other equivalent circuits (either alone or in combination with other digital or analog circuits).

Some illustrative embodiments of the present disclosure have been described above. However, it should be understood that various modifications can be made to the exemplary embodiments described above without departing from the spirit and scope of the present disclosure. For example, an appropriate result can be achieved if the described techniques are performed in a different order and/or if the components of the described system, architecture, apparatus, or circuit are combined in other manners and/or replaced or supplemented with additional components or equivalents thereof; accordingly, the modified other embodiments also fall within the protection scope of the claims.

What is claimed is:

1. An imaging system, comprising:
   a positioning image acquisition unit, configured to acquire a positioning image of a scanning object;
   a monitoring slice image acquisition unit, configured to obtaining a key point corresponding to the position of a target region of interest in the positioning image by using a neural network, and acquire a monitoring slice image of the scanning object at the position of the key point, wherein the key point is selected based on an anatomy of the target region of interest; and
   a target region-of-interest segmentation unit, configured to segment the monitoring slice image to obtain the target region of interest.

2. The imaging system according to claim 1, wherein the neural network comprises a residual neural network.

3. The imaging system according to claim 1, wherein the target region of interest is used to monitor a contrast agent concentration during a contrast scan.

4. The imaging system according to claim 1, wherein the target region-of-interest segmentation unit comprises a cascaded coarse segmentation unit and fine segmentation unit, wherein the coarse segmentation unit segments the monitoring slice image to obtain an initial region of interest, and the fine segmentation unit further segments the initial region of interest on the basis of the initial region of interest to obtain the target region of interest.

5. The imaging system according to claim 4, wherein the coarse segmentation unit performs coarse segmentation on the monitoring slice image by using at least one of a threshold method, an edge detection method, an erosion expansion method, a region growth method, a level set, or deep learning method; the fine segmentation unit performs fine segmentation on the monitoring slice image by using at least one of a morphological method, a threshold method, an edge detection method, an erosion expansion method, a region growing method, a level set, or deep learning method.

6. An imaging method, comprising:
   acquiring a positioning image of a scanning object;
   acquiring a monitoring slice image, by obtaining a key point corresponding to the position of a target region of interest in the positioning image by using a neural network, and acquiring the monitoring slice image of the scanning object at the position of the key point, wherein the key point is selected based on an anatomy of the target region of interest; and
   segmenting the monitoring slice image to obtain the target region of interest.

7. The method according to claim 6, wherein the neural network comprises a residual neural network.

8. The method according to claim 6, wherein the target region of interest is used to monitor a contrast agent concentration during a contrast scan.

9. The method according to claim 7, wherein the segmentation of the monitoring slice image to obtain the region of interest comprises: performing cascaded coarse segmentation and fine segmentation on the monitoring slice image, wherein the coarse segmentation segments the monitoring slice image to obtain an initial region of interest, and the fine segmentation further segments the monitoring slice image to obtain the target region of interest.

10. The method according to claim 9, wherein the coarse segmentation performs segmentation on the slice image by using at least one of a threshold method, an edge detection method, an erosion expansion method, a region growth method, a level set, or deep learning method to obtain the initial region of interest; the fine segmentation performs fine segmentation on the monitoring slice image by using at least one of a threshold method, an edge detection method, an erosion expansion method, a region growing method, a level set, or a deep learning method to obtain the target region of interest.

11. A system, comprising a processor configured to perform the method according to any one of claim 7.

* * * * *